(12) United States Patent
Reimels

(10) Patent No.: US 9,730,683 B2
(45) Date of Patent: Aug. 15, 2017

(54) BLADE ATTACHMENT AND ADJUSTMENT MECHANISM FOR TISSUE RETRACTION

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 41 days.

(21) Appl. No.: 14/457,581

(22) Filed: Aug. 12, 2014

(65) Prior Publication Data
US 2015/0045626 A1    Feb. 12, 2015

Related U.S. Application Data

(60) Provisional application No. 61/864,945, filed on Aug. 12, 2013.

(51) Int. Cl.
*A61B 17/02* (2006.01)
*A61B 17/00* (2006.01)

(52) U.S. Cl.
CPC ... *A61B 17/0206* (2013.01); *A61B 2017/00473* (2013.01); *A61B 2017/00477* (2013.01)

(58) Field of Classification Search
CPC .................................................. A61B 17/0206
USPC ......................................... 600/219–220, 224
See application file for complete search history.

(56) References Cited

U.S. PATENT DOCUMENTS

| | | | | |
|---|---|---|---|---|
| 6,224,545 B1 * | 5/2001 | Cocchia | ............... | A61B 1/32 600/233 |
| 6,569,091 B2 * | 5/2003 | Diokno | ............... | A61B 1/32 600/205 |
| 7,981,031 B2 * | 7/2011 | Frasier | ............... | A61B 17/02 600/224 |
| 8,357,184 B2 * | 1/2013 | Woolley | ............ | A61B 17/0206 600/210 |
| 8,882,661 B2 * | 11/2014 | Hutton | ............... | A61B 17/02 600/201 |
| 2002/0022771 A1 * | 2/2002 | Diokno | ............... | A61B 1/32 600/220 |
| 2006/0224044 A1 * | 10/2006 | Marchek | ............ | A61B 17/0293 600/233 |
| 2007/0038033 A1 * | 2/2007 | Jones | ................ | A61B 17/0293 600/219 |
| 2007/0043357 A1 * | 2/2007 | Kirschman | ........ | A61B 17/7032 606/266 |
| 2007/0156024 A1 * | 7/2007 | Frasier | ................ | A61B 17/02 600/219 |
| 2007/0208228 A1 * | 9/2007 | Pavento | ............. | A61B 17/0293 600/233 |
| 2008/0114208 A1 * | 5/2008 | Hutton | ............... | A61B 17/02 600/201 |
| 2009/0203969 A1 * | 8/2009 | Cohen | ............... | A61B 17/02 600/245 |

* cited by examiner

*Primary Examiner* — Jan Christopher Merene
(74) *Attorney, Agent, or Firm* — Dinsmore & Shohl LLP

(57) ABSTRACT

A blade assembly for a tissue retractor includes a blade, a mount, and a positioner member. The blade includes a length extending from a proximal portion with a coupling to a distal portion for retracting soft tissue. The mount includes a receiving portion that receives the coupling. The positioner member is rotatably coupled to the mount and engages the proximal portion to apply a force that positions the blade relative to the mount.

17 Claims, 12 Drawing Sheets

BLADE ATTACHMENT AND ADJUSTMENT MECHANISM FOR TISSUE RETRACTION

FIELD

The present disclosure generally relates to the field of spinal orthopedics, and more particularly to blade attachment and adjustment mechanisms for tissue retractors.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various surgical approaches to the spine including anterior, lateral, and posterior approaches.

In some circumstances, a tissue retractor may be inserted into a surgical incision to pull tissue away from the surgical site and enlarge the viewing area for the surgeon. Tissue retractors form a surgical corridor including a proximal opening at the incision and a distal opening near the surgical site. Various instruments and implants may be inserted through the corridor. Exemplary tissue retractors may be found in U.S. Pat. No. 7,780,594 entitled "Retractor and Methods of Use" filed Oct. 6, 2006 and U.S. App. Pub. No. 2008/0114208 entitled "Retractor" filed Sep. 24, 2007. The amount of tissue to be retracted depends upon the chosen approach as well as various patient characteristics. For example, in a lateral approach, more soft tissue may be present between the surgical incision and the surgical site near the vertebrae than in a posterior approach. Patient anatomical differences may also require various length retractors. The size, shape, and configuration of the retractor may be chosen based on these as well as other factors.

Tissue retractors typically include two or more elongated blade assemblies with proximal ends attached to a housing that is in turn attached to a surgical table for support. Each blade assembly may be attached to a separate portion of the housing and include various adjustment features for manipulating the blades to adjust and enlarge the viewing area. Often, the tissue retractor may hold the blades close together in a tubular configuration for concentric insertion over dilation tubes along a common longitudinal axis. The portions of the housing may translate or rotate relative to one another to gradually pull the blades apart from one another to expand the surgical opening. In addition, the distal ends of the retractor blades may be angled away from (toe-out) or towards (toe-in) the longitudinal axis to adjust the viewing area at the surgical site.

In order to perform a lateral surgical procedure to implant an interbody spacer, a soft tissue retractor similar to retractor 100 or 100' may be necessary in order to gain exposure through the psoas muscle. Often, a plurality of dilators is inserted into the patient to begin to open the surgical site. Typically, a 2-, 3-, or a 4-blade retractor system is slid over the dilators and used to expand the soft tissue to expose the surgical site allowing direct visualization for the implant procedure. Due to variances in human anatomy, the retractor must accommodate a range of interchangeable blades of different lengths. In addition, the retractor system should provide the ability to tilt the distal ends of the blades radially outward to create a toe-out condition that provides greater exposure of the surgical site near the spine.

Most systems require retractor removal to change the blades. Therefore, when it is discovered that a different blade length is necessary after insertion, changing the blades may be cumbersome and risk tissue encroachment. Further, most systems employ separate mechanisms for blade attachment and toe out which complicates installation and manipulation of the blades by the user. Further, existing toe-out mechanisms allow blade tilting in only discreet steps, typically of 5, 10, and 15 degrees. Since the blade lengths can be as long as 160 mm, these increments cause large displacement at the distal end of the blade which leads to over distraction of muscle tissue. Last, many blade coupling mechanisms are insufficiently strong and secure to resist the high bending loads generated as the blades are expanded or under toe-out conditions and the tissue resists the expansion.

SUMMARY

A blade assembly for a tissue retractor includes a blade, a mount, and a positioner member. The blade includes a length extending from a proximal portion with a coupling to a distal portion for retracting soft tissue. The mount includes a receiving portion that receives the coupling. The positioner member is rotatably coupled to the mount and engages the proximal portion to apply a force that positions the blade relative to the mount.

In other features, the coupling forms an axis of rotation extending transverse to the length of the blade. The receiving portion includes slots with proximally-facing openings that receive the coupling.

In still other features, the positioner member includes an outer surface having an outer radius from a longitudinal axis of the positioner member and a height extending parallel to the longitudinal axis. The positioner member includes a first recessed portion in the outer surface at a first radius that is less than the outer radius. The positioner member includes a second recessed portion in the outer surface at a second radius that is less than the outer radius and greater than the first radius. The positioner member includes a third recessed portion in the outer surface at a third radius that is less than the outer radius and that extends along a portion of the height of the positioner member.

In yet other features, the first recessed portion receives a blade tang of the proximal portion and the receiving portion includes a slot that receives the coupling. The second recessed portion applies a force on a blade tang of the proximal portion and the receiving portion includes a slot that receives the coupling to guide translation of the blade radially. Third recessed portion applies a force on a blade tang of the proximal portion and the receiving portion includes a slot that receives the coupling to guide rotation of the blade about the coupling.

In yet other features, the positioner member rotates about a longitudinal axis relative to the mount to engage a recessed portion with the proximal portion to translate the blade relative to the mount. In yet other features, the positioner member rotates about a longitudinal axis relative to the mount to engage a recessed portion with the proximal portion to rotate the blade relative to the mount.

In another example, a blade assembly for a tissue retractor includes a blade, a mount, and a positioner member. The blade includes a length extending from a proximal portion with a blade tang and a coupling to a distal portion for retracting soft tissue. The mount includes a receiving portion with slots that receives the coupling. The positioner member includes a longitudinal axis of rotation relative to the mount and an outer surface at an outer radius from the longitudinal axis. The positioner member is rotatably coupled to the mount to engage recessed portions in the outer surface with the blade tang to translate and rotate the blade relative to the mount.

In other features, each of the slots includes a proximally-facing opening for receiving the coupling, a first portion for guiding translation of the coupling distally, a second portion for guiding translation coupling radially, and a closed end for guiding rotation of the blade about the coupling.

In still other features, the recessed portions include a first recessed portion at a first radius less than the outer radius for receiving the blade tang while the first portion of the slots guide translation of the blade distally via the coupling, a second recessed portion at a second radius less than the outer radius and greater than the first radius for applying a force to translate the blade tang radially as the second portion of the slots guides translation of the blade radially via the coupling, and a third recessed portion at a third radius less than the outer radius and extending along a height of the positioner member for applying a torque to the blade tang to rotate the blade about the coupling as the closed end guides rotation of the blade.

In another example, a retractor for retracting soft tissue includes a perimeter portion and at least one blade assembly that includes a blade, a mount, and a positioner member. The blade includes a length extending from a proximal portion with a blade tang and a coupling to a distal portion for retracting soft tissue. The mount includes a receiving portion with slots that receives the coupling. The positioner member is rotatably coupled to the mount and engages the blade tang to apply a force that positions the blade relative to the mount.

In other features, the coupling forms an axis of rotation extending transverse to the length of the blade and the slots receive the coupling and guide translation and rotation of the blade relative to the mount. In still other features, the positioner member includes an outer surface having an outer radius from a longitudinal axis of the positioner member and a height extending parallel to the longitudinal axis, wherein the positioner member includes a first recessed portion in the outer surface at a first radius that is less than the outer radius that receives the blade tang.

In yet other features, the positioner member includes a second recessed portion in the outer surface at a second radius that is less than the outer radius and greater than the first radius that translates the blade radially. The positioner member includes a third recessed portion in the outer surface at a third radius that is less than the outer radius and that extends along a portion of a height of the positioner member that rotates the blade about the coupling.

DETAILED DESCRIPTION

Accordingly, the blade attachment and adjustment system of the present disclosure includes a tool-less, quick connect blade attachment mechanism that also functions as a blade adjustment mechanism with infinitely variable blade toe-in adjustment. The system may be used with a variety of styles of retractors to spread the blades apart prior to the toe-in adjustment. The system includes various features to simplify the user interface by combining the blade attachment and adjustment requirements into a single, resilient quick connect mechanism that allows infinite adjustment of the toe-out angle.

The system eliminates the need for additional mechanical joints between the blades and the retractor which could lead to additional sources of failure. The system incorporates a quick connect feature that allows the blade to be introduced from a superior position such that the blade can be interchanged in-situ around a dilator. The locking feature allows free adjustment of the toe-out angle and constant locking over the entire range from 0 to at least 15 degrees.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
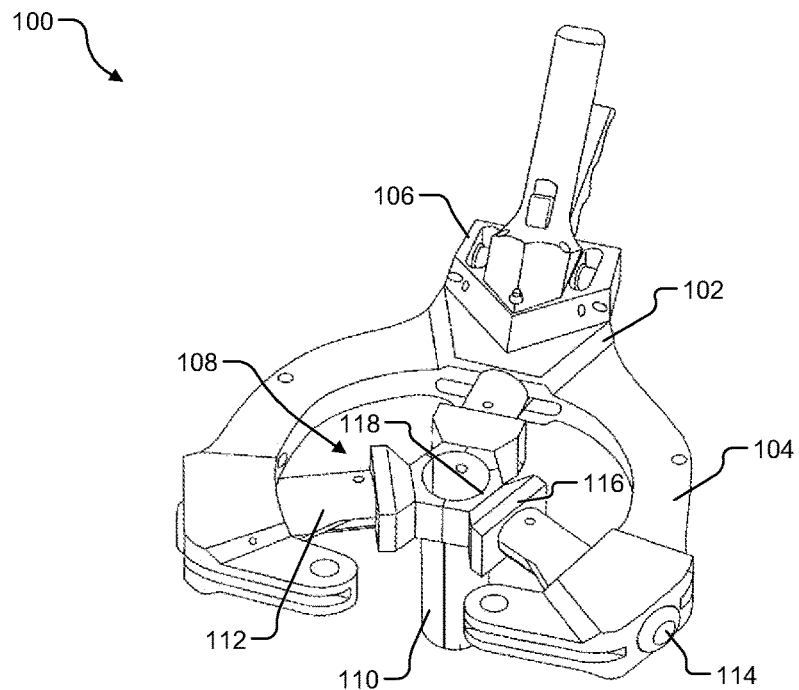
FIG. 1 is a perspective view of a first exemplary tissue retractor system.
Figure 2:
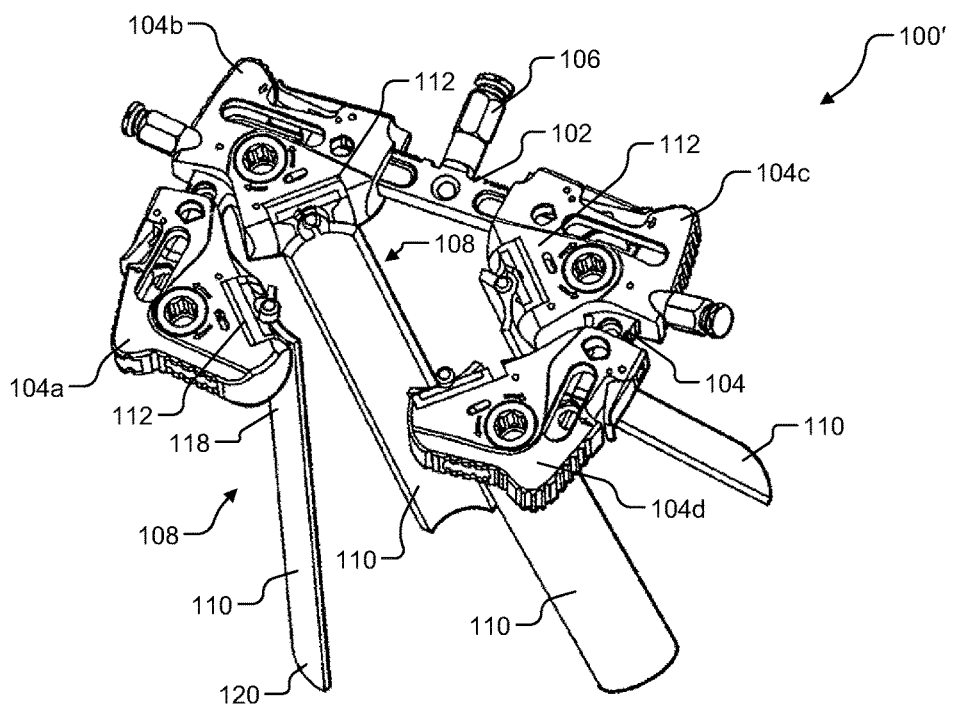
FIG. 2 is a perspective view of a second exemplary tissue retractor system.

Referring to FIGS. 1 and 2, exemplary tissue retractor systems 100 and 100' may include housings 102 of various forms. For example, in FIG. 1, the housing 102 may include a rigid perimeter portion 104, comprising a generally C-shaped configuration, with an attachment feature 106 for attaching to various styles of surgical table arms. The attachment feature 106 may include a clamp, setscrew, or other removable table attachment feature, such as those described in U.S. Pat. No. 7,780,594. Three retractor blade assemblies 108 may couple with the perimeter portion 104. Each blade assembly 108 may include a retractor blade 110 and mount 112. Each mount 112 includes a first end 114 for coupling with the perimeter portion 104 and a second end 116 for coupling with a proximal portion 118 of the retractor blade 110.

In some exemplary tissue retractors systems, such as retractor system 100' shown in FIG. 2, the relative position of the blade assemblies 108 to one another may be adjusted through translation of individual sections 104a-d of the perimeter portion 104 of the housing 102. For example, the blade assemblies 108 may be translated apart from one another to enlarge the proximal opening formed by the blades 110. Each mount 112 of the blade assemblies 108 may couple with a separate section 104a-104d of the perimeter portion 104. The mounts 112 may include various other features to enable rotation or pivoting of the blades 110 relative to the housing 102 to enlarge the distal opening formed by the blades 110. For example, the mounts 112 may include gear systems that allow a surgeon to adjust the toe-in or toe-out of distal ends 120 of the blades 110 similar to the systems described in U.S. App. Pub. No. 2008/0114208. Increasing the toe-out by pivoting the distal ends 120 of the blades 110 radially outward, as shown in FIG. 2, increases the viewing area at the surgical site near the distal ends 120 during a surgical procedure.

Figure 3:
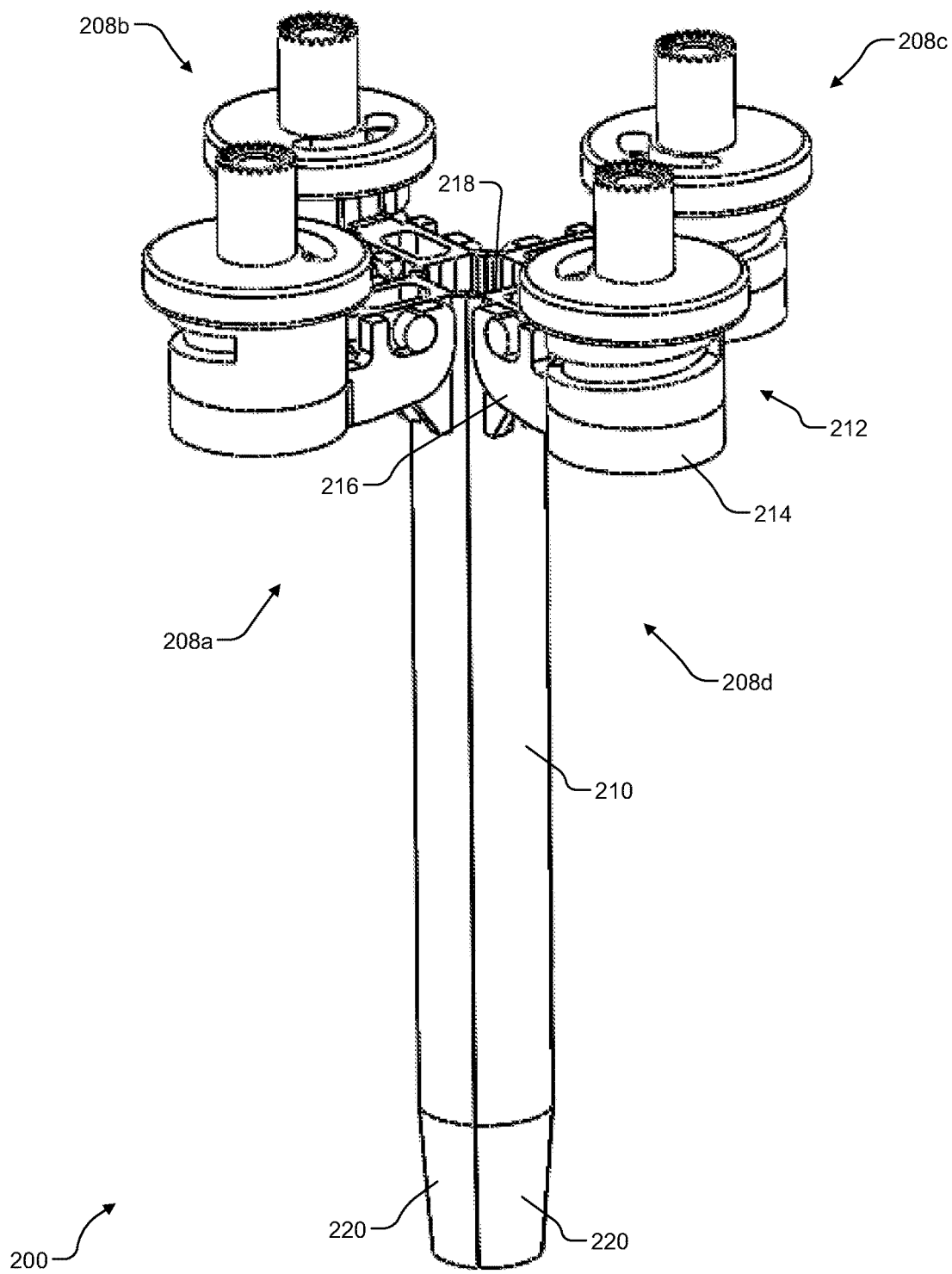
FIG. 3 is a perspective view of an exemplary system for attachment and adjustment of retractor blades to a tissue retractor system according to the principles of the present disclosure.

Referring now to FIG. 3, a system 200 for attachment and adjustment of retractor blades relative to a retractor is shown. The system 200 may include two or more blade assemblies 208, each independently adjustable. It may be understood by one of ordinary skill in the art that the system 200 may include two, three, four, or more blade assemblies 208. For example, the system 200 may comprise three blade assemblies 208 that may be attached to the perimeter 104 of the retractor system 100 of FIG. 1 or such as the retractor system disclosed in U.S. Pat. No. 7,207,949. The system 200 may include two blade assemblies 208 for attachment to other styles of retractors. For ease of discussion, the system 200 is described below with reference to a four blade assembly retractor system.

In the present example, the system 200 includes first, second, third, and fourth blade assemblies, 208a, 208b, 208c, and 208d (collectively blade assemblies 208) which may be configured for attachment to the perimeter portion 104 of the retractor system 100' shown in FIG. 2. For ease of discussion, one blade assembly may be described generically as blade assembly 208. In some examples, the system 200 may include identical blade assemblies 208. In other examples, the system 200 may not include identical blade assemblies 208. However, the system 200 includes at least one blade assembly 208 with similar features as described herein.

The blade assembly 208 includes a retractor blade 210 and a mount 212. The mount 212 includes a first end 214 for coupling with the perimeter portion 104 of a retractor assembly such as retractor assembly 100 or 100' and a second end 216 for coupling with a proximal portion 218 of the retractor blade 210. Each blade 210 includes a distal end 220 for insertion through the surgical incision to the surgical site. The four blade assemblies 208 may be permanently or removably attached, for example only, to the four sections 104a, 104b, 104c, and 104d respectively of the perimeter portion 104 of the retractor system 100' of FIG. 2.

Figure 4:
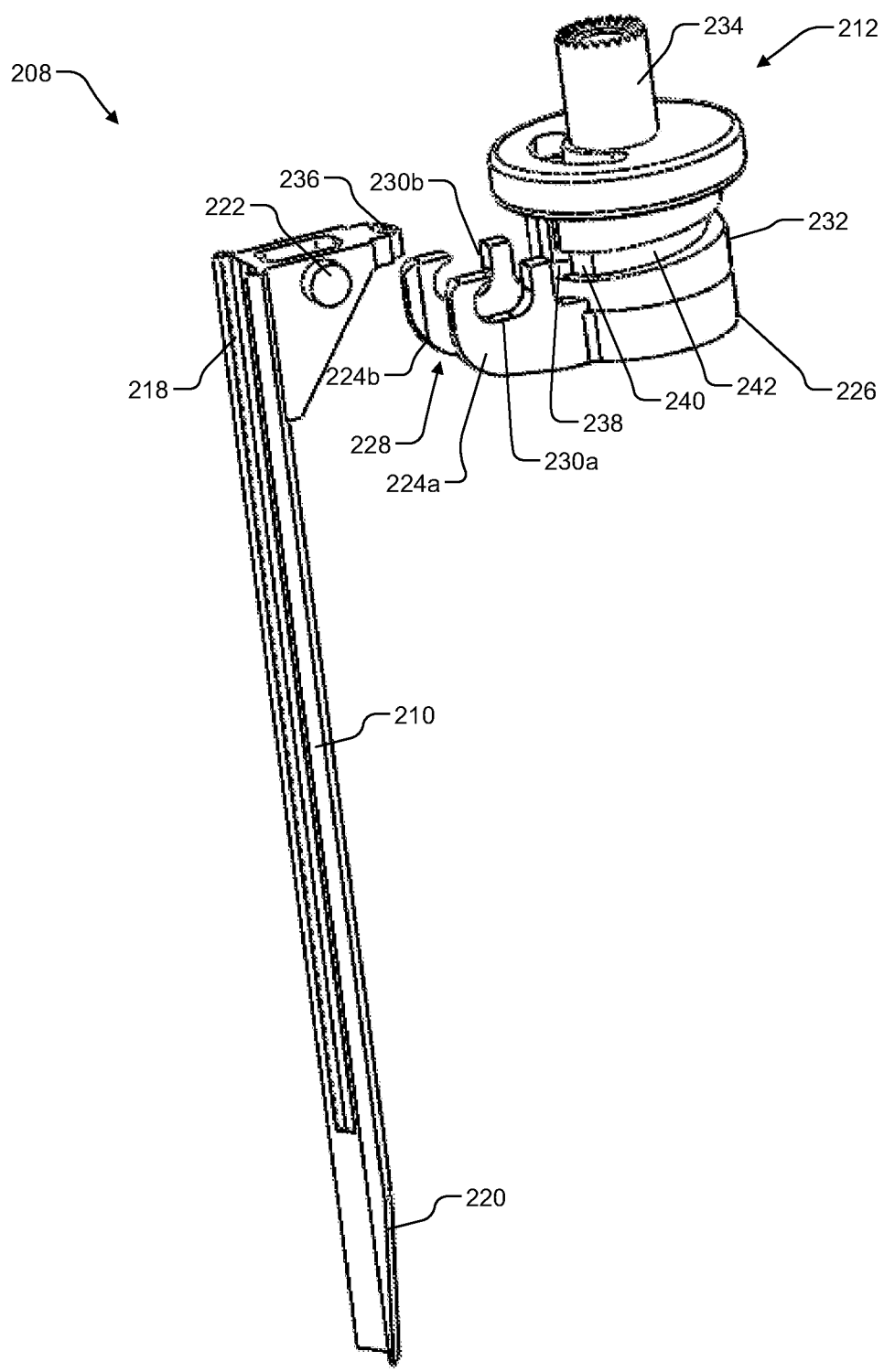
FIG. 4 is a perspective view of an exemplary blade assembly of the system of FIG. 3 according to the principles of the present disclosure.
Figure 5:
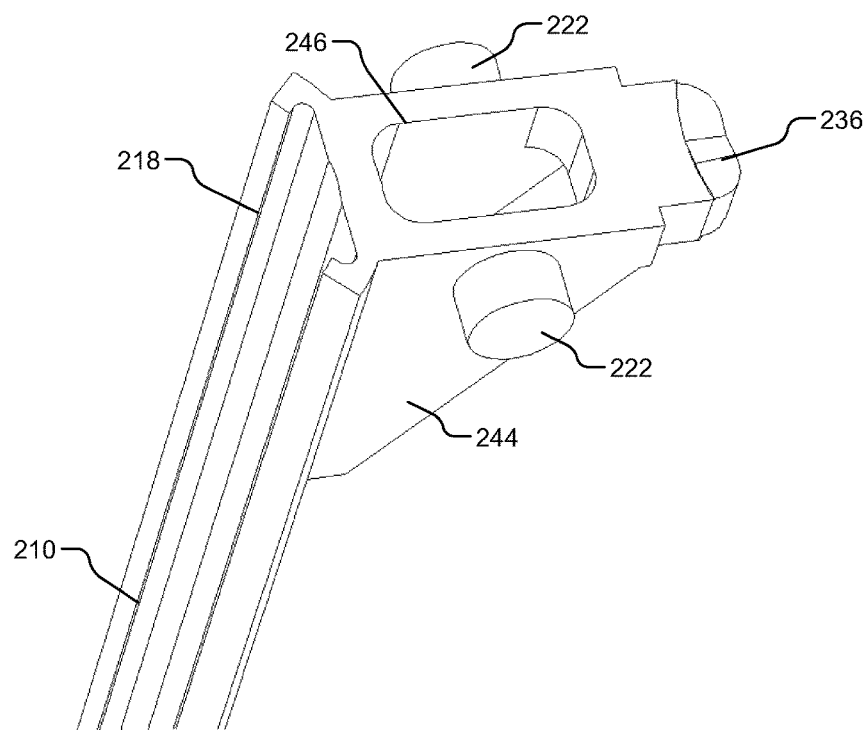
FIG. 5 is a partial perspective view of a proximal end of an exemplary blade of the blade assembly of FIG. 4 according to the principles of the present disclosure.
Figure 6:
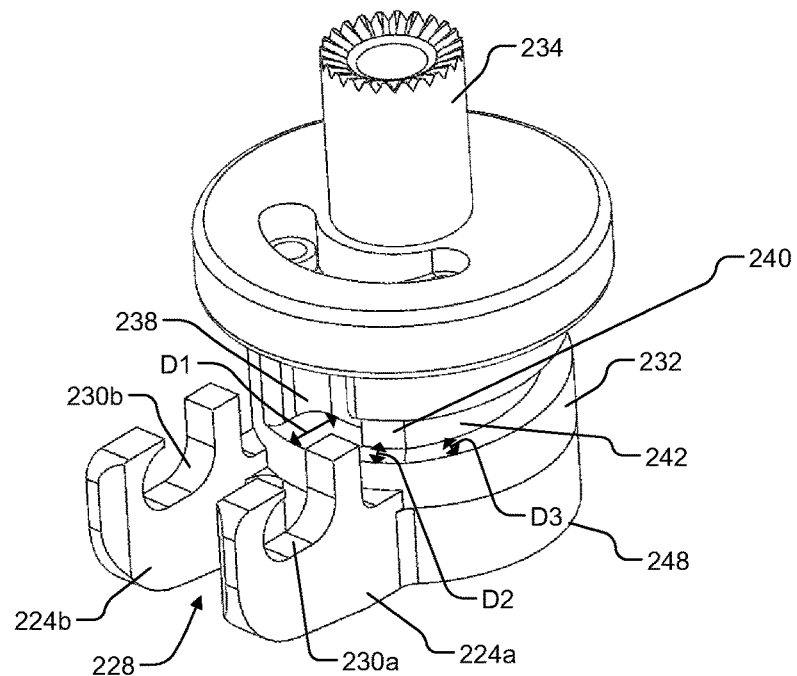
FIG. 6 is a perspective view of an exemplary mount of the blade assembly of FIG. 4 according to the principles of the present disclosure.

Continuing now with FIGS. 4-6, the blade assembly 208 includes various features that facilitate easy insertion and removal of the blade 210 prior to and after insertion into a patient, locking the blade 210 in place, and adjusting the toe-out angle of the distal end 220 of the blade 210. For example, the mount 212 may include a quick-connect feature that allows fast, reliable coupling of the blade 210 and simultaneously permit pivoting or rotating of the blade 210 to adjust toe-out and toe-in angles. The mount 212 may include a blade receiving portion at the second end 216 that receives the proximal portion 218. The proximal portion 218 of the blade 210 may include rotatable coupling 222, such as bosses or other projections extending transverse to the length of the blade 210, so as to form an axis of rotation about which the length of the blade 210 may rotate. The blade receiving portion may include a pair of arms 224a and 224b (collectively arms 224) extending away from a base portion 226 of the mount 212. An opening 228 formed by or in between the arms 224 may receive the proximal portion 218 of the blade 210. A pair of slots 230a and 230b (collectively slots 230) within the arms 224 may receive the bosses 222 as the blade 210 is inserted distally between the arms 224. Translation and rotation of the blade 210 relative to the mount 212 may occur via the bosses 222 sliding within the slots 230.

The blade assembly 208 further includes a positioner member 232 rotatably coupled with a shaft 234 of the mount 212. The positioner member 232 includes features that engage with the proximal portion 218 to lock the blade 210 in place and adjust the toe-out angle of the distal end 210 of the blade. For example, the proximal portion 218 may include a toe adjustment feature, such as a blade tang 236 that extends substantially perpendicular to the bosses 222 and the length of the blade 210. Upon insertion of the proximal portion 218 into the opening 228, the blade tang 236 may begin to engage one or more features of the positioner member 232. These features may be used to receive the blade tang 236, transfer a translating force on the blade tang 236 to translate/position the blade 210 into locking arrangement with the arms 224, and transfer a torque on the blade tang 236 to pivot/rotate the blade 210 and adjust the toe-out or toe-in angle.

The positioner member 232 may include a spool that rotates about the shaft 234. For example, the positioner member 232 may include a substantially cylindrical body with a longitudinal axis of rotation. The cylindrical body may include an outer radius R at an outer surface, a height H, and a number of recessed portions at various depths from the outer surface that engage or receive the blade tang 236 and position the blade tang 236 relative to the mount 212. The recessed portions may be located along a length of the spool from a proximal end to a distal end along a longitudinal axis of the spool. The positioner member 232 may rotate about the mount 212 to position the various recessed portions into engagement with the blade tang 236.

Referring to FIG. 6, the positioner member 232 may include a first recessed portion 238 with a first depth D1 from an outer surface of the positioner member 232. The first recessed portion 238 may loosely receives the blade tang 236 once inserted. The first recessed portion 238 may include a pocket or channel configured to approximate the shape of the blade tang 236. The depth D1 may correspond to a dimension of the slots 230 such that as the positioner member 232 rotates, the first recessed portion 238 may transition to a second recessed portion 240 with a second depth D2 less than the first depth D1.

Therefore, as the positioner member 232 rotates, the first recessed portion 238 transitions to the second recessed portion 240 to engage the blade tang 236 and force the proximal portion 218 away from the mount 212 causing the bosses 222 to advance within the slots 230 by a distance of D2. In this manner, the bosses 222 may be secured in a portion of the slots 230 as described in greater detail below. Thus, the positioner member 232 may be configured to receive the blade tang 236 and lock the blade proximal portion 218 within the slots 230.

As the positioner member 232 continues to rotate, the second recessed portion 240 may transition into a third recessed portion 242 with substantially the same depth D3. However, the third recessed portion 242 may be formed into a spiral slot, helical channel, or other feature circumscribed in the outer surface along the length of the spool. As the positioner member 232 rotates, the third recessed portion 242 applies a force on the blade tang 236 to rotate the blade 210 about the bosses 222 within the slots 230. For example, a distal surface of the third recessed portion 242 may pull proximally on the blade tang 236 as the spiral slot rotates in a first direction. A proximal surface of the third recessed portion 242 may push distally on the blade tang 236 as the spiral slot rotates in an opposite second direction. In this manner, the positioner member 232 may increase or decrease the toe-in/toe-out of the distal end 220 of the blade. The third recessed portion 242 may also provide a constant locking force as the blade 210 is positioned due to the screw-like engagement of the spiral slot and the blade tang 236.

Continuing with FIG. 5, the proximal portion 218 of the blade 210 may experience high levels of mechanical stress due to forces applied by the positioner member 232. The proximal portion 218 of the blade 210 may include a strengthened portion 244, which may include one or more gusset plates or other structural enhancements, to increase material strength near the proximal portion 218. An opening 246 within the strengthened portion 244 may provide a view to the surgical area along an outer surface of the blade 210. The opening 246 may allow access for various neurological monitoring probes, devices, and fixation elements for securing the blade 210 to the surgical area, for example, by attachment to the intervertebral disc and/or adjacent vertebrae. The bosses 222 may be formed from the strengthened portion 244 as a pair of cylindrical projections extending substantially perpendicular to the length of the blade 210 and the length of the blade tang 236. The blade tang 236 may include a tab or projection that extends away from the proximal portion 218 towards the mount 212 when assembled. The blade tang 236 may extend substantially perpendicular to and in a shared plane with the bosses 222. The interior and exterior sides of the blade 210 may include various channels, slots, and tracks configured to receive blade extensions, blade fixation mechanisms, instruments, implants, probes, or other devices.

Referring to FIG. 6, the blade-receiving portion includes the arms 224a and 224b (collectively arms 224) that extend away from a base portion 248. The base portion 248 may include a substantially circular/cylindrical configuration with the arms 224 extending parallel to a segment or chord of the circular cross-section. Alternatively, the arms 224 may extend radially or tangentially away from the base portion 248. The arms 224 may form the opening 228 therebetween to receive the proximal portion 218 of the blade 210. Each of the arms 224a and 224b may include the respective slot 230a and 230b (collectively slots 230) for receiving the bosses 222. The blade 210 may translate and rotate or pivot about the bosses 222 within the slots 230. The slots 230 may include a J-shaped configuration with proximal openings in the arms 224 such that the blade 210 may be inserted distally through the slots 230 and then advanced radially away from a longitudinal axis of the mount 212 into a closed ends of the slots 230.

Referring now also to FIGS. 7A-7D, side views of the proximal end of the blade assembly 208 illustrate steps for insertion and coupling of the blade 210 with the mount 212. Vertical direction corresponds In FIG. 7A, the slot 230 includes a generally "J" shaped configuration with a proximally-facing slot opening 250 for receiving the boss 222. The slot 230 may include a first portion 252 extending distally from the slot opening 250 that transitions to a second portion 254 extending radially from the first portion 252. The first portion 252 may include a substantially vertical portion. The second portion 254 may include a substantially non-vertical portion. The second portion 254 may terminate in a closed end 256 to retain the boss 222 within the slot 230. The closed end 256 may include curvature that partially encloses or wraps around the boss 222. For example, the closed end 256 may include a generally cylindrical profile that mates with the boss 222.

Figures 7A, 7B:
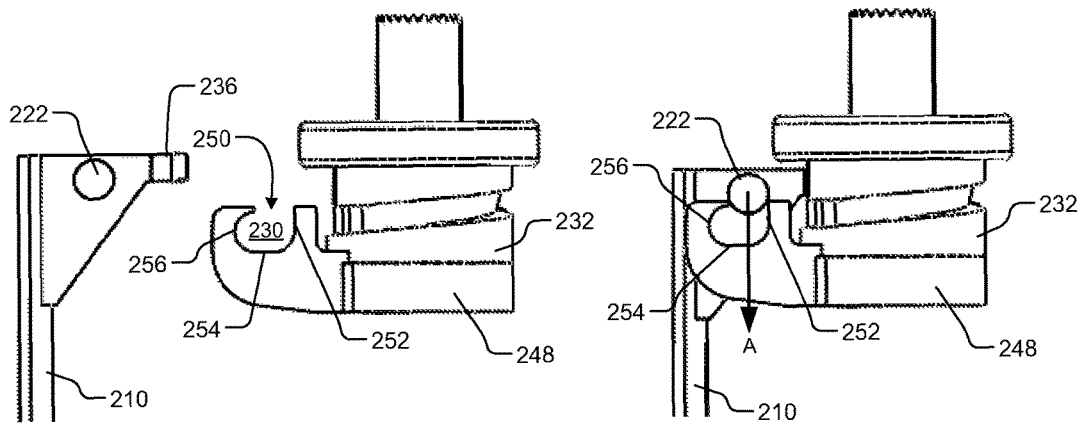
FIGS. 7A-7D are side views illustrating insertion of the blade of FIG. 5 into the mount of FIG. 4 according to the principles of the present disclosure.
Figures 7C, 7D:
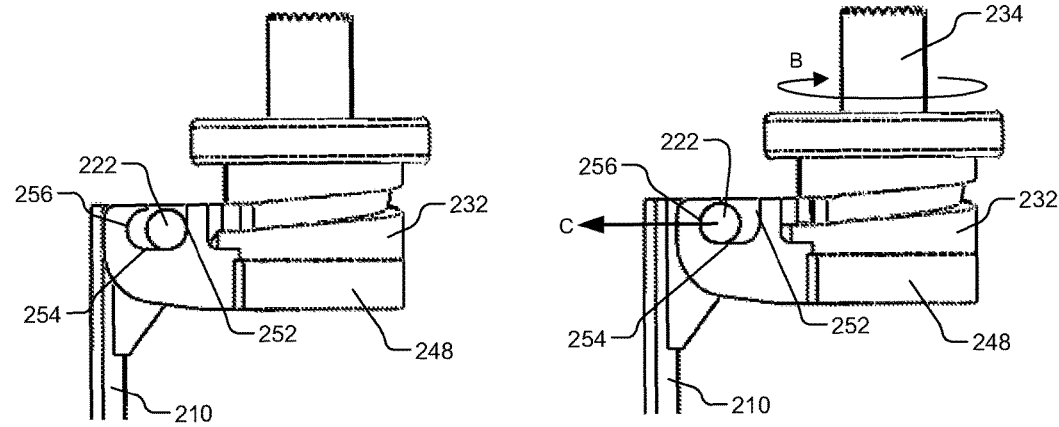

The slot 230 permits insertion of the blade 210 into the mount 212 by sliding the boss 222 distally through the slot opening 250 and along the first portion 252 as illustrated by arrow A in FIG. 7B. The blade tang 236 may be accommodated by the first recessed portion 238 within the positioner member 232. As the blade 210 advances distally, the boss 222 may slide along the first portion 252 until reaching the second portion 254 as shown in FIG. 7C. Once seated on the second portion 254, the positioner member 232 may then be rotated about the shaft 234 as illustrated by arrow B to engage the second recessed portion 240 with the blade tang 236 and translate boss 222 along the second portion 254 as illustrated by arrow C and into contact with the closed end 256 as shown in FIG. 7D.

In the exemplary embodiment of FIGS. 7A-7D, the slot 230 is shown as including a substantially vertical first portion 252 and a substantially non-vertical second portion 254 as well as an overall J-shaped profile. However, other examples of the slot 230 may include various angles of inclination and shapes. For example, the first portion 252 may include a slight inclination or ramp that may position the blade 210 towards the positioner member 232 to facilitate locking. The slight inclination or ramp may position the blade 210 away from the positioner member 232 to facilitate locking. Similarly, the second portion 254 may include a slight inclination or ramp that may position the blade 210 distally or proximally within the slot 230.

Figure 8A:
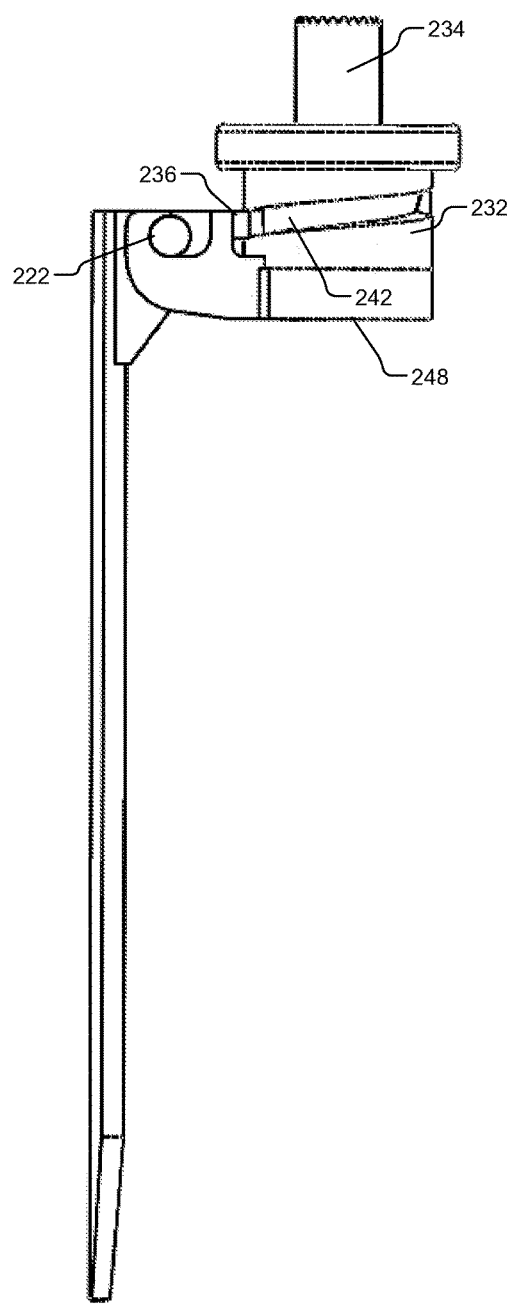
FIGS. 8A-8D are side views illustrating adjustment of the blade of FIG. 5 by actuation of features of the mount of FIG. 6 according to the principles of the present disclosure.
Figure 8B:
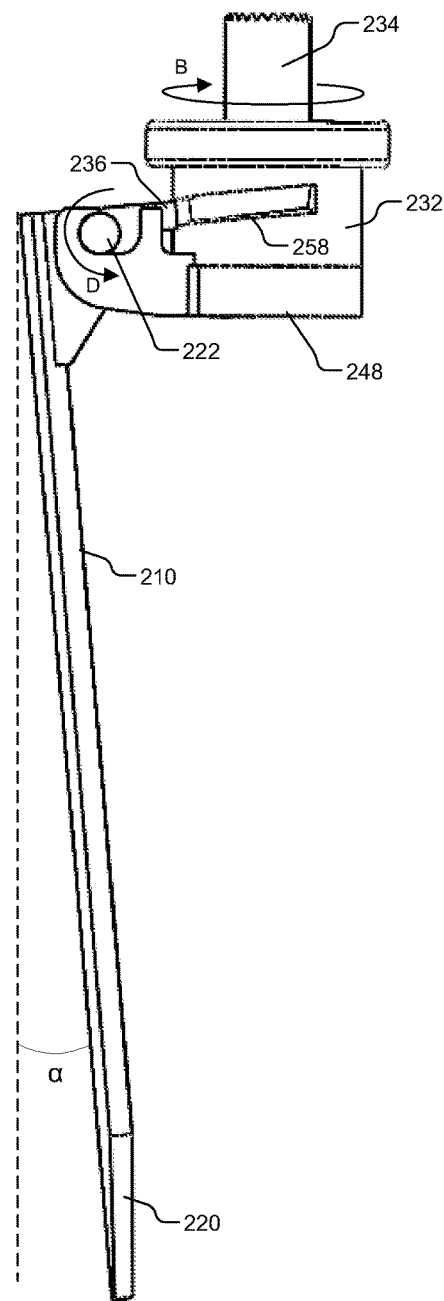
Figure 8C:
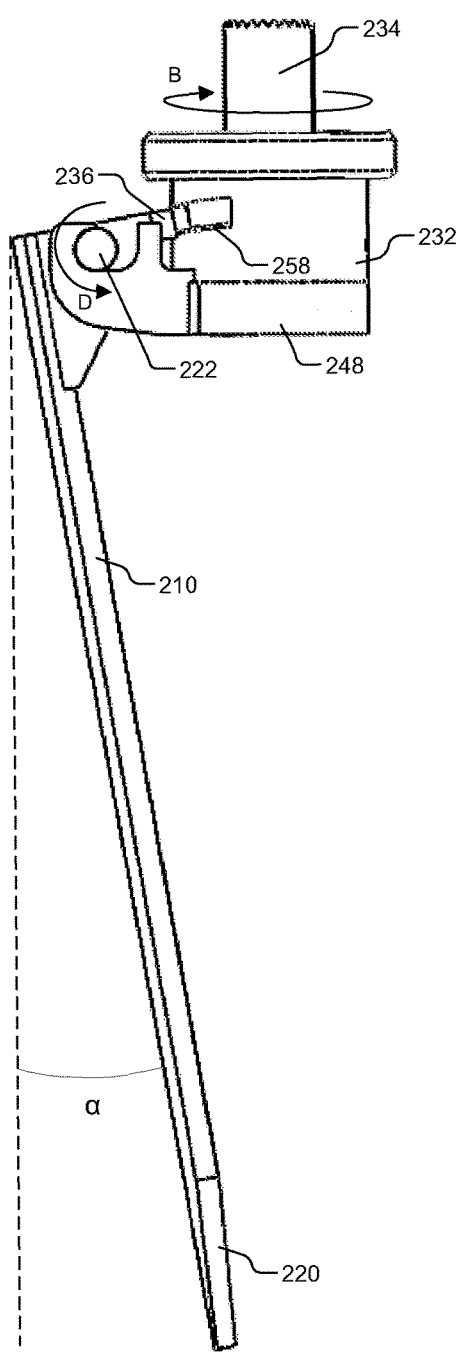
Figure 8D:
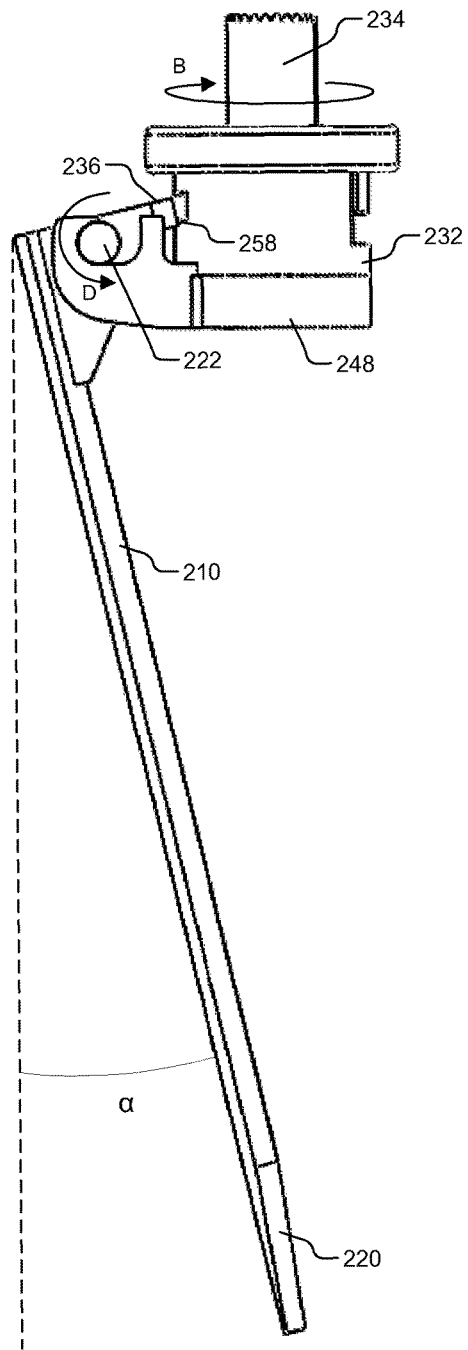

Once the blade 210 has been inserted into the mount 212 in an inserted position, as shown in FIG. 8A, the positioner member 232 may continue to be rotated to actuate the blade 210 and adjust a toe-out angle α thereby positioning the distal end 220 radially outward from the surgical site as shown in FIGS. 8B-8D. The toe-out angle α may be infinitely adjustable from an insertion angle of approximately 0 degrees at the insertion position of to a maximum angle corresponding to dimensions of the recessed portions in the positioner member 232. For example, as illustrated in FIGS. 8A-8D, the third recessed portion 242 may include a spiral slot 242 that engages with the blade tang 236. As the positioner member 232 continues to rotate in the direction of arrow B, the blade tang 236 is forced proximally due to engagement with a lower surface 258 of the slot 242. The lower surface 258 pushes the blade tang 236 proximally by applying a torque. The blade 210 begins to rotate about the bosses 222 in the direction denoted by arrow D. The angle α may be infinitely adjusted by rotating the spool 222 to any position. The lower surface 258 also provides a self-locking force similar to a worm gear or other threaded-engagement self-lock mechanisms.

Figure 9:
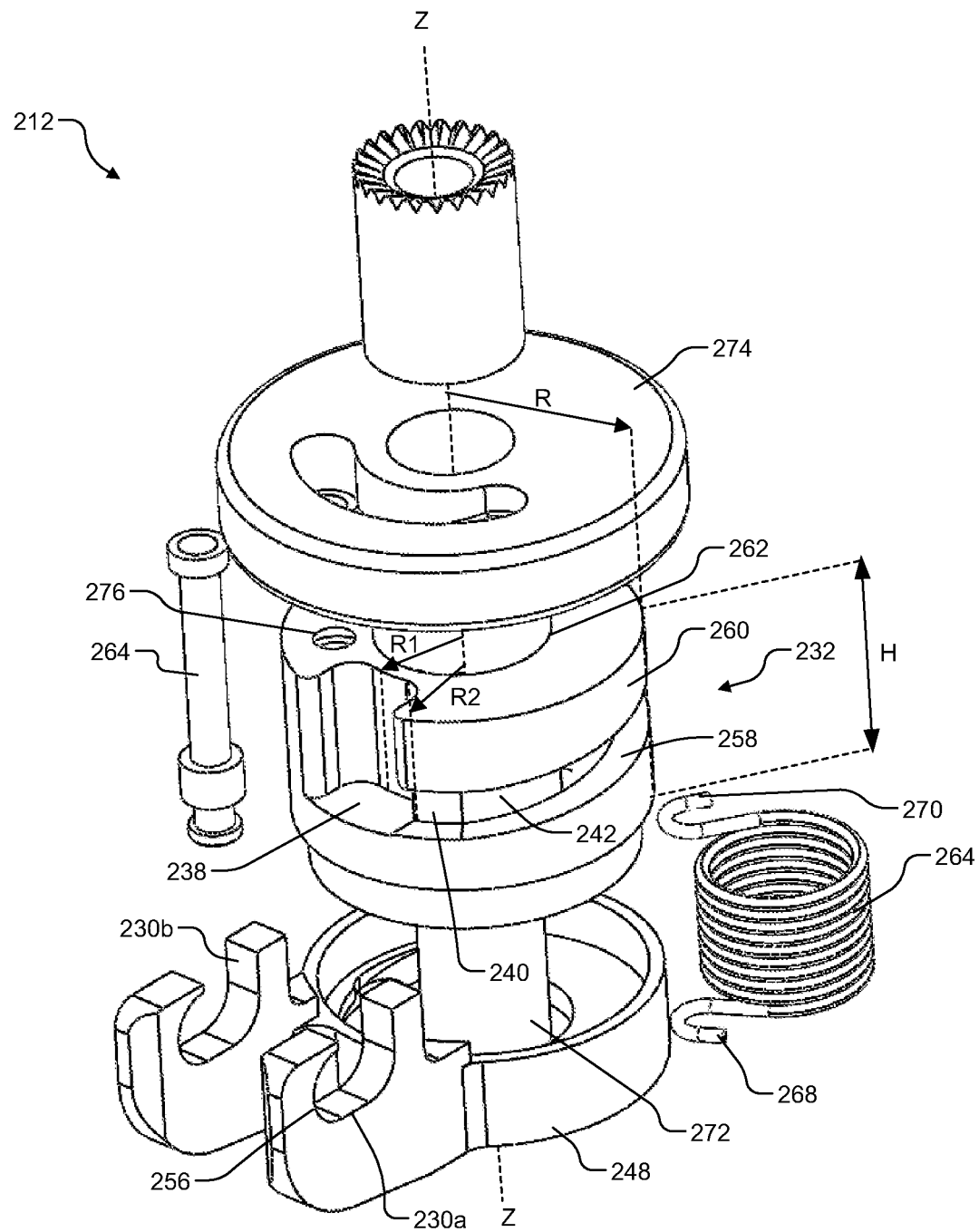
FIG. 9 is an exploded perspective view of the mount of FIG. 6 according to the principles of the present disclosure.

Referring now to FIG. 9, an exploded view of the mount 212 illustrates additional features for positioning of the positioner member 232 used to actuate the blade 210. The positioner member 232 may include a generally cylindrical outer surface 260 and may include a thru-bore 262 that receives the shaft 234. A portion of the outer surface 260 includes a varying profile to engage the blade tang 236 and position the blade 210 as described above. For example, the outer surface 260 232 may be disposed at radial distance R from the longitudinal axis Z of the positioner member 232. The first recessed portion 238 may be disposed at a first radius R1 from the longitudinal axis Z to form a pocket sufficient to loosely receive the blade tang 236. For example, R1 may be substantially the same as the outer surface radius R less the depth D1 of the first recessed portion 238. As the positioner member 232 rotates, the first recessed portion 238 may transition to another recess or channel that applies a force to lock the bosses 222 within the closed ends 256 of the slots 230.

As the positioner member 232 rotates, the first recessed portion 238 may transition to the second recessed portion 240 which may be a locking recess. The second recessed portion 240 may be disposed at a second radius R2 from the longitudinal axis Z that is greater than the first radius R1. For example, R2 may be substantially the same as the outer surface radius R less the depth D2 of the second recessed portion 240. The increase in radius causes engagement between the positioner member 232 and the blade tang 236. The positioner member 232 may apply a force on the blade tang 236 to translate the blade 210 radially away from the positioner member 232 and into locking engagement with the ends 256 of the slots 230. In some examples, a transition zone or chamfered edge may separate transition the first recessed portion 238 into the second recessed portion 240.

As the positioner member 232 continues to rotate, additional features may begin to apply a torque to pivot the bosses 222 within the slots 230. For example, the third recessed portion 242, shown as spiral slot 242, may wrap around a portion of the outer surface 260 in a helical or threaded pattern along a length of the outer surface running parallel to the longitudinal axis Z. The third recessed portion 242 may include a depth from the outer surface 260 corresponding to the second radius R2 measured from the longitudinal axis Z. Alternately, the third recessed portion 242 may include varying depths or radii corresponding to specific toe-out angles. Thus, the spiral slot 242 may form a continuous channel in the outer surface 260 having a uniform or varying depth. The spiral slot 242 may include any number of thread patterns including helical, ramped, corkscrew, and the like with varying angles to the lower surface 258.

Figure 10:
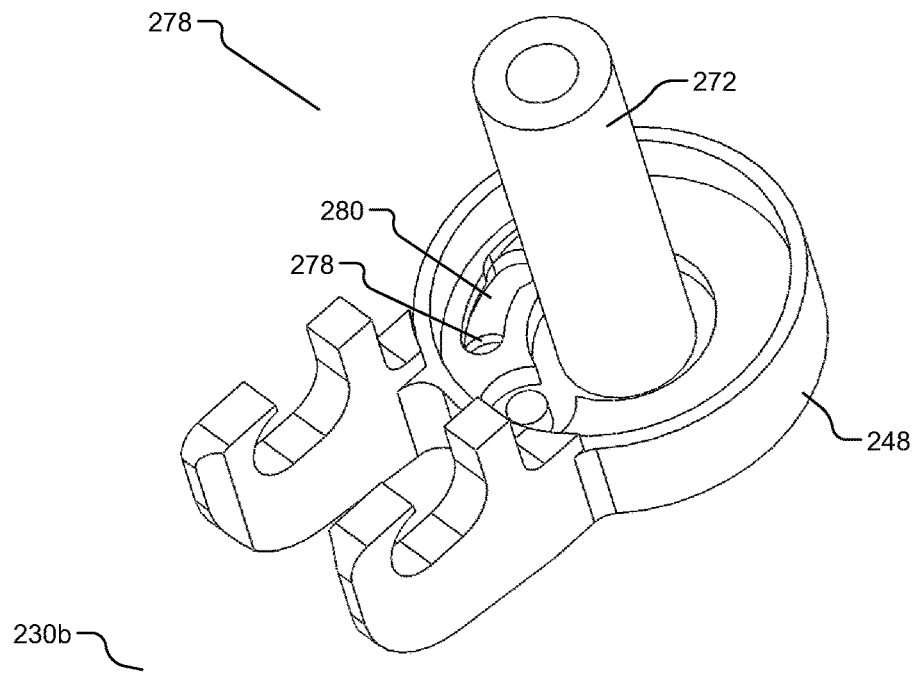
FIG. 10 is a perspective view of a portion of the mount of FIG. 6 according to the principles of the present disclosure.
Figure 11:
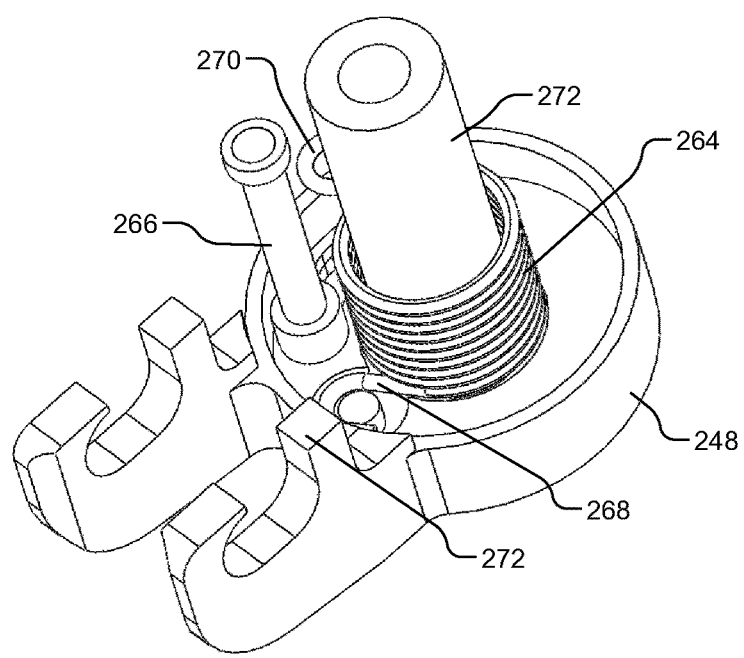
FIG. 11 is a perspective view of a portion of the mount of FIG. 6 including internal features according to the principles of the present disclosure.

Referring now also to FIGS. 10 and 11, the mount 212 may include various features that assist with positioning the blade 210 and retaining or locking the positioner member 232 at predetermined points of rotation. For example, the mount 212 may include a torsion spring 264 and a detent pin 266. The torsion spring 264 may include a first end 268 that couples with the base portion 248 of the mount 212 and a second end 270 that couples with the positioner member 232. The torsion spring 264 may be disposed around a mount shaft 272 that extends through a portion of the bore 262 of the positioner member 232. The torsion spring 264 may be pre-loaded to prevent the positioner member 232 from creeping back after the user has set the toe-out angle α.

In addition, the detent pin 266 may work collectively with a series of ramps, bores, recesses, and channels within the base portion 248, the positioner member 232, and a control knob 274 to lock the positioner member 232 at various stages or rotation. The positioner member 232 may include a detent bore 276 that slidingly receives the detent pin 266. Although not shown, a bias spring may be disposed around the detent pin 266 within the detent bore 276 to bias the detent pin 266 distally. The base portion 248 may include first recess 278 that receives the distal end of the pin 266 when the first recessed portion 238 of the positioner member 232 is aligned to receive the blade 210. The base portion 248 may include a second recess 280 that receives the distal end 282 of the pin 266 when the second recessed portion 240 of the positioner member 232 engages the blade tang 236 to lock the bosses 222 within the slots 230.

Figure 12A:
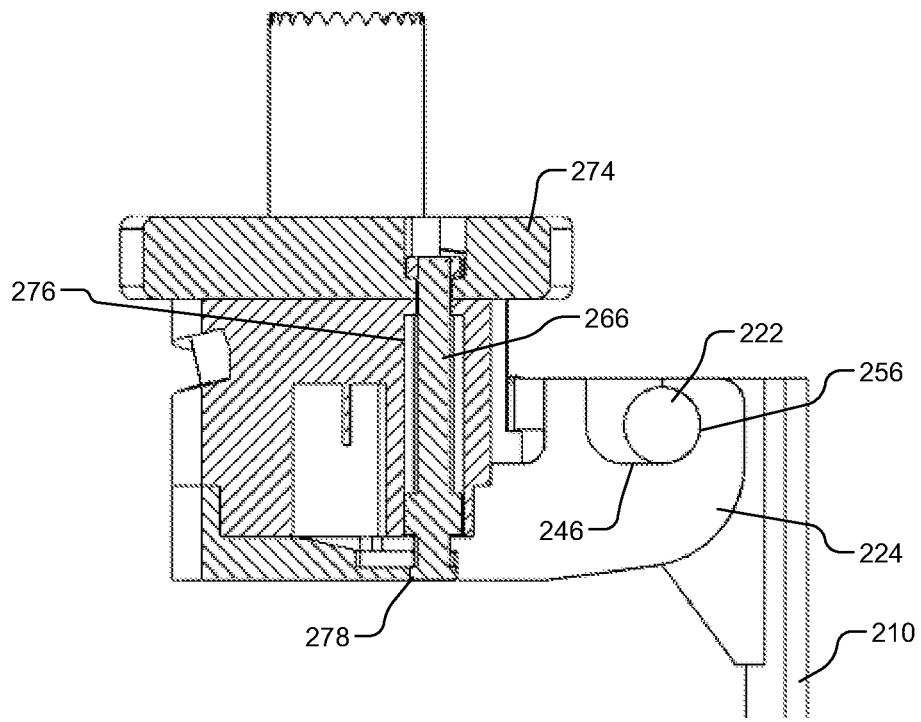
FIGS. 12A-E are partial cross-sectional views of the blade assembly according to the principles of the present disclosure.

Interaction between the detent pin 266, base portion 248, positioner member 232, and control knob 274 may be more readily understood in cross-sectional views illustrated in FIGS. 12A-12E. In FIG. 12A, the boss 222 of the blade 210 has been inserted into the slot 230 of the arm 224. Although the blade 210 is shown positioned radially outward such that the boss 222 contacts the end 256 of the slot 230, the proximal end 218 may be free to slide along the non-vertical portion 246 of the slot 230. The blade tang 236 may be disposed within the first recessed portion 238 of the positioner member 232. In this open position, the positioner member 232 may be open to receive and release the proximal end 218 of the blade. In the open position, the distal end 282 of the detent pin 266 may be disposed within the first recess 278.

Figure 12B:
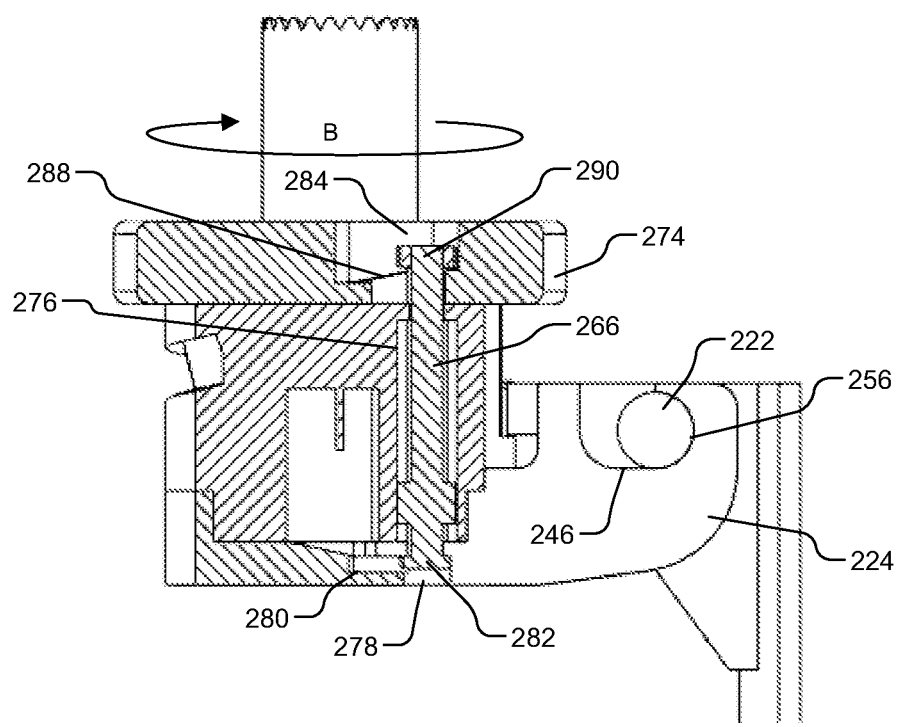
Figure 12C:
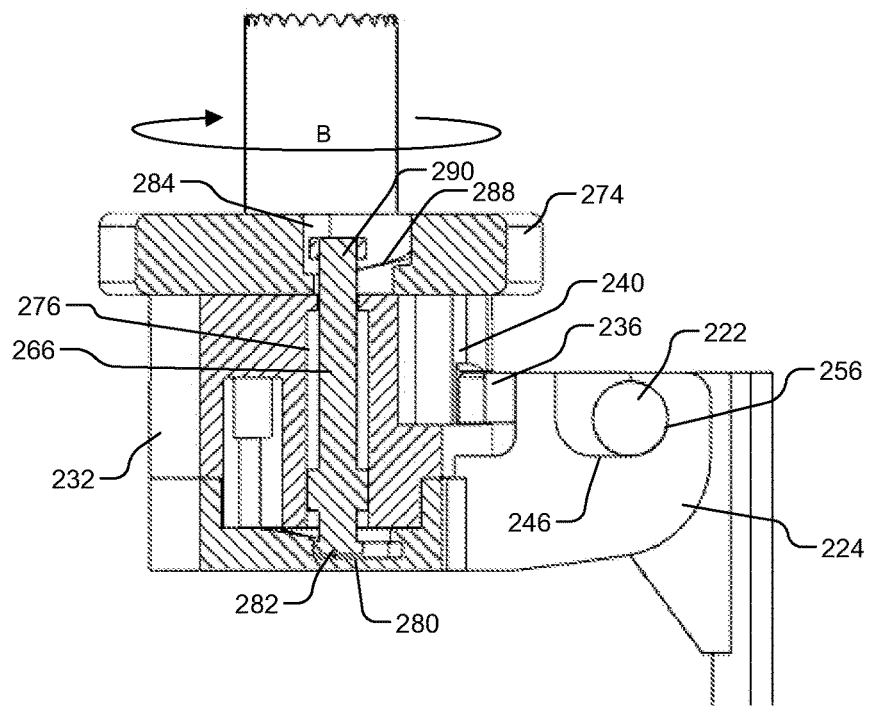

Continuing now with FIG. 12B, the control knob 274 may be rotated in the direction of arrow B to release the detent pin 266 from the first recess 278. The control knob 274 may include a slot 284 with a ramp 288 that engages with a proximal end 290 of the detent pin 266. As the control knob 274 rotates, the ramp 288 pulls the pin 266 proximally to release the distal end 282 from the first recess 278. The control knob 274 may continue to rotate as shown in FIG. 12C. The slot 284 may apply a force on the proximal end 290 of the detent pin 266 causing the pin 266 to rotate with the control knob 274. The detent pin 266 may transfer the force to the positioner member 232 due to engagement with the detent bore 276 causing the positioner member 232 to rotate as well. Thus, the positioner member 232 may rotate to engage the second recessed portion 240 with the blade tang 236 to lock the bosses 222 within end 256 of the slot 230. The distal end 282 of the detent pin 266 may engage with the second recess 280 to hold the blade 210 in an initial position with a toe-out angle of 0 degrees.

Figure 12D:
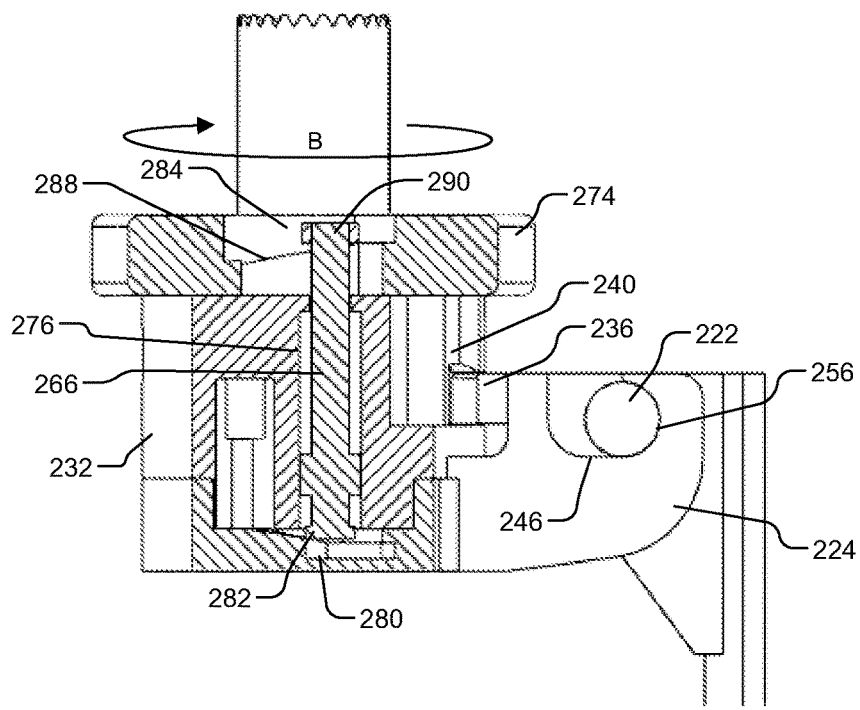
Figure 12E:
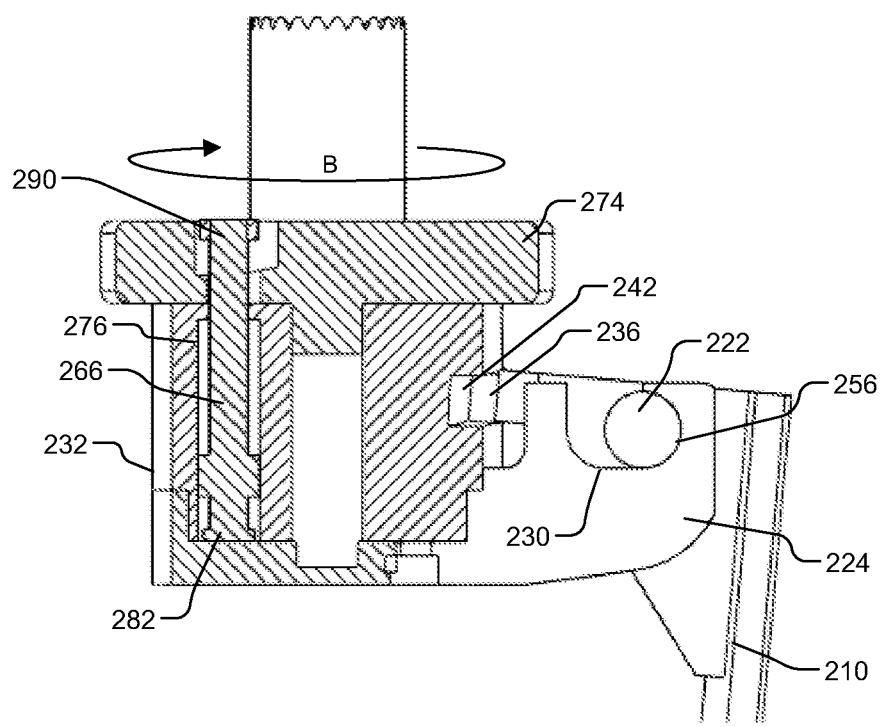

Referring now to FIG. 12D, the control knob 274 may continue to be rotated to release the detent pin 266 from the second recess 280. The ramp 288 pulls the pin 266 proximally to release the distal end 282 from the second recess 280. Once the distal end 282 has been released from the second recess 280, the control knob 274 may continue to be rotated as shown in FIG. 12E. The slot 284 may apply a force on the proximal end 290 of the detent pin 266 causing the pin 266 to rotate with the control knob 274. The detent pin 266 may transfer the force to the positioner member 232 due to engagement with the detent bore 276 causing the positioner member 232 to rotate as well. Thus, the positioner member 232 may rotate to engage the third recessed portion 242 with the blade tang 236 and begin to rotate the blade 210 about the bosses 222 as described above. The third recessed portion 242 may provide infinitely variable toe-out angles for the blades 210.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A blade assembly for a tissue retractor, comprising:
   a blade having a length extending from a proximal portion with a coupling to a distal portion for retracting soft tissue;
   a mount including a receiving portion that receives the coupling, the receiving portion having a pair of arms, each of the pair of arms having a generally J-shaped slot, the J-shaped slots having a proximal-facing opening, an elongated opening and a medial closed end opposite a radiused front end so as to define a lip, the elongated opening extending between the medial closed end and the radiused front end so as to be generally orthogonal to the blade and having a length longer than the proximal opening, wherein the proximal opening is configured to receiving the coupling, the lip extending above the radiused front end so as to cover the radiused front end and wherein the lip is co-planar with the proximal opening, wherein the proximal-facing opening is configured to receive the blade and wherein the lip and radiused front end work in concert with each other to lock the blade within the J-shaped slots; and
   a positioner member rotatably coupled to the mount that engages the proximal portion to apply a force that positions the blade relative to the mount.

2. The blade assembly of claim 1, wherein the coupling forms an axis of rotation extending transverse to the length of the blade.

3. The blade assembly of claim 1, wherein the positioner member includes an outer surface having an outer radius from a longitudinal axis of the positioner member and a height extending parallel to the longitudinal axis.

4. The blade assembly of claim 3, wherein the positioner member includes a first recessed portion in the outer surface at a first radius that is less than the outer radius.

5. The blade assembly of claim 4, wherein the positioner member includes a second recessed portion in the outer surface at a second radius that is less than the outer radius and greater than the first radius.

6. The blade assembly of claim 5, wherein the positioner member includes a third recessed portion in the outer surface at a third radius that is less than the outer radius and that extends along a portion of the height of the positioner member.

7. The blade assembly of claim 4, wherein the first recessed portion receives a blade tang of the proximal portion.

8. The blade assembly of claim 5, wherein the second recessed portion applies a force on a blade tang of the proximal portion and the receiving portion includes a slot that receives the coupling to guide translation of the blade radially.

9. The blade assembly of claim 6, wherein the third recessed portion applies a force on a blade tang of the proximal portion and the receiving portion includes a slot that receives the coupling to guide rotation of the blade about the coupling.

10. The blade assembly of claim 1, wherein the positioner member rotates about a longitudinal axis relative to the mount to engage a recessed portion with the proximal portion to translate the blade relative to the mount.

11. The blade assembly of claim 1, wherein the positioner member rotates about a longitudinal axis relative to the mount to engage a recessed portion with the proximal portion to rotate the blade relative to the mount.

12. A blade assembly for a tissue retractor, comprising:
    a blade having a length extending from a proximal portion with a blade tang and a coupling to a distal portion for retracting soft tissue;
    a mount including a receiving portion having a generally J-shaped slot, the J-shaped slot having a proximal-facing opening, a radiused front end, and a medial closed end for receiving and locking the blade; and
    a positioner member including a longitudinal axis of rotation relative to the mount and an outer surface at an outer radius from the longitudinal axis, the positioner member rotatably coupled to the mount to engage recessed portions in the outer surface with the blade tang to translate and rotate the blade relative to the mount, wherein the recessed portions include:
    a first recessed portion at a first radius less than the outer radius for receiving the blade tang while the J-shaped slot guides translation of the blade distally via the coupling,
    a second recessed portion at a second radius less than the outer radius and greater than the first radius for applying a force to translate the blade tang radially as the J-shaped slot guides translation of the blade radially via the coupling, and
    a third recessed portion at a third radius less than the outer radius and extending along a height of the positioner member for applying a torque to the blade tang to rotate the blade about the coupling as the radiused front end guides rotation of the blade.

13. A retractor for retracting soft tissue, comprising:
a perimeter portion configured for attachment to a surgical table arm; and at least one blade assembly attached to the perimeter portion that includes
a blade having a length extending from a proximal portion with a blade tang and a coupling to a distal portion for retracting soft tissue;
a mount including a receiving portion, the receiving portion having a pair of arms, each of the pair of arms having a slot that receives the coupling, the slots being generally J-shaped and having a proximal-facing opening and a medial closed end opposite a radiused front end so as to define a lip, the lip extending above the radiused front end so as to cover the radiused front end, and wherein the lip is co-planar with the proximal opening, wherein the proximal-facing opening is configured to receive the blade and wherein the lip and radiused front end work in concert with each other to lock the blade within the slots; and
a positioner member rotatably coupled to the mount that engages the blade tang to apply a force that positions the blade relative to the mount.

14. The blade assembly of claim 13, wherein the coupling forms an axis of rotation extending transverse to the length of the blade and the slots receive the coupling and guide translation and rotation of the blade relative to the mount.

15. The blade assembly of claim 13, wherein the positioner member includes an outer surface having an outer radius from a longitudinal axis of the positioner member and a height extending parallel to the longitudinal axis, wherein the positioner member includes a first recessed portion in the outer surface at a first radius that is less than the outer radius that receives the blade tang.

16. The blade assembly of claim 15, wherein the positioner member includes a second recessed portion in the outer surface at a second radius that is less than the outer radius and greater than the first radius that translates the blade radially.

17. The blade assembly of claim 16, wherein the positioner member includes a third recessed portion in the outer surface at a third radius that is less than the outer radius and that extends along a portion of a height of the positioner member that rotates the blade about the coupling.

* * * * *